United States Patent [19]
Shuber

[11] Patent Number: 5,888,778
[45] Date of Patent: Mar. 30, 1999

[54] HIGH-THROUGHPUT SCREENING METHOD FOR IDENTIFICATION OF GENETIC MUTATIONS OR DISEASE-CAUSING MICROORGANISMS USING SEGMENTED PRIMERS

[75] Inventor: Anthony P. Shuber, Milford, Mass.

[73] Assignee: Exact Laboratories, Inc., Maynard, Mass.

[21] Appl. No.: 877,333

[22] Filed: Jun. 16, 1997

[51] Int. Cl.⁶ ............... C12P 19/34; C07H 21/04; C07H 21/00; C12N 15/00
[52] U.S. Cl. ............... 435/91.1; 435/91.2; 536/24.33; 536/25.1; 536/25.3; 935/76; 935/77
[58] Field of Search ............... 435/6, 91.1, 91.2, 435/183; 536/23.1, 24.3, 24.31, 24.33, 25.3; 935/8, 26, 77; 436/94

[56] References Cited

U.S. PATENT DOCUMENTS

| 5,200,313 | 4/1993 | Carrico | 435/6 |
| 5,202,231 | 4/1993 | Drmanac et al. | 435/6 |
| 5,545,527 | 8/1996 | Stevens et al. | 435/6 |
| 5,552,283 | 9/1996 | Diamandis et al. | 435/6 |
| 5,571,676 | 11/1996 | Shuber | 435/6 |
| 5,578,458 | 11/1996 | Caskey et al. | 435/6 |
| 5,589,330 | 12/1996 | Shuber | 435/5 |

FOREIGN PATENT DOCUMENTS

| 0 332 435 A2 | 9/1989 | European Pat. Off. . |
| 0 332 435 B1 | 9/1989 | European Pat. Off. . |
| 0 408 918 A1 | 1/1991 | European Pat. Off. . |
| 0 408 918 B1 | 1/1991 | European Pat. Off. . |
| 0 497 527 A1 | 8/1992 | European Pat. Off. . |
| WO 91/13075 | 9/1991 | WIPO . |
| WO 92/15712 | 9/1992 | WIPO . |
| WO 95/00669 | 1/1995 | WIPO . |
| WO 95/12607 | 5/1995 | WIPO . |
| WO 96/30545 | 10/1996 | WIPO . |

OTHER PUBLICATIONS

Sommer and Tautz, "Minilam homology requirements of PCR primers," Nucleic Acids Research, vol. 17, No. 16, p. 6749, 1989.
Caetano–Anollés (1993) Amplifying DNA with Arbitrary Oligonucleotide Primers, *PCR Methods and Applications*, 3:85–94.
Krook, et al., (1992) Rapid and simulataneous detection of multiple mutations . . . in non–insulin–dependent diabetes, *Human Molecular Genetics*, 1:391–395.
Shumaker, et al., (1996) Mutation Detection by Solid Phase Primer Extension, Human Mutation, 7:346–354.
Ikonen, et al., (1992) Quantitative Determination of Rare mRNA Species by PCR and Solid–phase Minisequencing, *PCR Methods and Applications* 1:234–240.

(List continued on next page.)

*Primary Examiner*—Bradley L. Sisson
*Attorney, Agent, or Firm*—Testa, Hurwitz & Thibeault LLP

[57] ABSTRACT

Methods are provided for high-throughput screening for the presence of genetic alterations and disease-causing microorganisms in a biological sample. These methods are particularly useful for identifying individuals with gene mutations indicative of early colorectal cancer.

15 Claims, 1 Drawing Sheet

OTHER PUBLICATIONS

Runnebaum, et al., (1994) Multiplex PCR Screeing detects small p53 deletions and insertions in human ovarian cancer cell lines, *Human Genetics,* 93:620–624.

Lebacq, (1992) Polymerase chain reaction and other methods to detect hot–spot and multiple gene mutations, *Ann Biol Clin,* 50:709–712.

Syvänen, (1994) Detection of point mutations in human genes by the solid–phase minisequencing method, *Clinica Chimica Acta,* 226:225–236.

Caldas, et al., (1994) Detection of K–ras Mutations in the Stool of Patients with Pancreatic Adenorcarcinoma and Pancreatic Ductal Hyperplasia, *Cancer Research,* 54:3568–3573.

Villa, et al., (1996) Identification of Subjects at Risk for Colorectal Carcinoma Through a Test Base on K–ras Determination in the Stool, *Gastroenterology,* 110:1346–1353.

Hasegawa, et al., (1995) Detection of K–ras mutations in DNAs isolated from feces of patients with colorectal tumors by mutant–allele–specific amplification (MASA), *Onogene,* 10:1441–1445.

Smith–Ravin, et al., (1995) Detection of c–Ki–ras mutations in feacal samples from sporadic colorectal cancer patients, *Gut,* 36:81–86.

Eguchi, et al., (1996) Mutations of the p53 Gene in the Stool of Patients with Resectable Colorectal Cancer, *Cancer Suppl.,* 77:1707–1710.

Nollau, et al., (1996) Detection of K–ras Mutations in Stools of Patients with Colorectal Cancer by Mutant–Enriched PCR, *Int. J. Cancer,* 66:332–336.

Kieleczawa, et al., (1992) DNA Sequencing by Primer Walking with Strings of Contiguous Hexamers, *Science,* 258:1787–1791.

Fu, et al., (1995) A DNA Sequencing Strategy That Requires Only Five Bases of Known Terminal Sequence for Priming, *Proc. Natl. Acad. Sci. USA,* 92:10162–10166.

Kotler, et al., (1993) DNA Sequencing: Modular Primers Assembled from a Library of Hexamers or Pentamers, *Proc. Natl. Acad. Sci. USA,* 90:4241–4245.

5,888,778

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1:

ACCAGCTCCA ACTACCACAA GTTTAT    26

( 2 ) INFORMATION FOR SEQ ID NO:2:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2:

ATAAACTTGT GGTAG    15

( 2 ) INFORMATION FOR SEQ ID NO:3:

( i ) SEQUENCE CHARACTERISTICS:
  ( A ) LENGTH: 8 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:3:

TTGGAGCT    8

( 2 ) INFORMATION FOR SEQ ID NO:4:

-continued (i) SEQUENCE CHARACTERISTICS:
    (A) LENGTH: 8 base pairs
    (B) TYPE: nucleic acid
    (C) STRANDEDNESS: single
    (D) TOPOLOGY: linear (x i) SEQUENCE DESCRIPTION: SEQ ID NO:4:

TGGAGCTG    8

(2) INFORMATION FOR SEQ ID NO:5:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (x i) SEQUENCE DESCRIPTION: SEQ ID NO:5:

ATAAACTTGT GGTAGTT    17

(2) INFORMATION FOR SEQ ID NO:6:

(i) SEQUENCE CHARACTERISTICS:
    (A) LENGTH: 8 base pairs
    (B) TYPE: nucleic acid
    (C) STRANDEDNESS: single
    (D) TOPOLOGY: linear (x i) SEQUENCE DESCRIPTION: SEQ ID NO:6:

GGAGCTGG    8

(2) INFORMATION FOR SEQ ID NO:7:

(i) SEQUENCE CHARACTERISTICS:
    (A) LENGTH: 8 base pairs
    (B) TYPE: nucleic acid
    (C) STRANDEDNESS: single
    (D) TOPOLOGY: linear (x i) SEQUENCE DESCRIPTION: SEQ ID NO:7:

ATAAACTT    8

(2) INFORMATION FOR SEQ ID NO:8:

(i) SEQUENCE CHARACTERISTICS:
    (A) LENGTH: 8 base pairs
    (B) TYPE: nucleic acid
    (C) STRANDEDNESS: single
    (D) TOPOLOGY: linear (x i) SEQUENCE DESCRIPTION: SEQ ID NO:8:

TGGTAGTT    8

HIGH-THROUGHPUT SCREENING METHOD FOR IDENTIFICATION OF GENETIC MUTATIONS OR DISEASE-CAUSING MICROORGANISMS USING SEGMENTED PRIMERS

FIELD OF THE INVENTION

This invention relates generally to methods for using segmented oligonucleotides. Methods of the invention are especially useful for disease diagnosis by detecting and identifying genetic mutations or the presence of disease-causing microorganisms in biological samples.

BACKGROUND OF THE INVENTION

The knowledge of molecular defects causative of diseases, such as inherited disorders and cancer, is increasing rapidly. Inherited diseases thought to be caused by genetic mutations include sickle cell anemia, α- and β-thalassemias, phenylketonuria, hemophilia, $α_1$-antitrypsin deficiency, and cystic fibrosis. Sickle cell anemia, for example, is reported to result from homozygosity resulting from a single base pair substitution in the sixth codon of the β-globin gene. Antonarakis, *New England J. Med.,* 320: 153–163 (1989). Mutations in the insulin receptor gene and in the insulin-responsive glucose transporter gene have been detected in insulin-resistant diabetes. Krook et al., *Human Molecular Genetics,* 1: 391–396 (1992).

Cancer has been associated with genetic mutations in a number of oncogenes and tumor suppressor genes. Duffy, *Clin. Chem.,* 41: 1410–1413 (1993). For example, point mutations in the ras genes have been shown to convert those genes into transforming oncogenes. Bos et al., *Nature,* 315: 726–730. Mutations and the loss of heterozygosity at the p53 tumor suppressor locus have been correlated with various types of cancer. Ridanpaa et al., *Path. Res. Pract.,* 191: 399–402 (1995); Hollstein et al., *Science,* 253: 49–53 (1991). In addition, the loss or other mutation of the apc and dcc tumor suppressor genes has also been associated with tumor development. Blum, *Europ. J. Cancer,* 31A: 1369–1372 (1995). Those mutations can serve as markers for early stages of disease and for predisposition thereto. Early diagnosis is not only important for successful treatment, but can also lead to prevention or treatment before chronic symptoms occur.

Colorectal cancer is an example of a disease that is highly curable if detected early. With early detection, colon cancer may be effectively treated by, for example, surgical removal of the cancerous tissue. Surgical removal of early-stage colon cancer is usually successful because colon cancer begins in cells of the colonic epithelium and is isolated from the general circulation during its early stages. Thus, detection of early mutations in colorectal cells would greatly increase survival rate. Current methods for detection of colorectal cancer focus on extracellular indicia of the presence of cancer, such as the presence of fecal occult blood or carcinoembryonic antigen circulating in serum. Such extracellular indicia typically occurs only after the cancer has become invasive. At that point, colorectal cancer is very difficult to treat.

Methods have been devised to detect the presence of mutations within disease-associated genes. One such method is to compare the complete nucleotide sequence of a sample genomic region with the corresponding wild-type region. See, e.g., Engelke et al., *Proc. Natl. Acad. Sci, U.S.A.,* 85: 544–548 (1988); Wong et al., *Nature,* 330: 384–386 (1988). However, such methods are costly, time consuming, and require the analysis of multiple clones of the targeted gene for unambiguous detection of low-frequency mutations. As such, it is not practical to use extensive sequencing for large-scale screening of genetic mutations.

A variety of detection methods have been developed which exploit sequence variation in DNA using enzymatic and chemical cleavage techniques. A commonly-used screen for DNA polymorphisms consists of digesting DNA with restriction endonucleases and analyzing the resulting fragments by means of southern blots, as reported by Botstein et al., *Am. J. Hum. Genet.,* 32: 314–331 (1980) and White et al., *Sci. Am.,* 258: 40–48 (1988). Mutations that affect the recognition sequence of the endonuclease will preclude enzymatic cleavage at that site, thereby altering the cleavage pattern of the DNA. Sequences are compared by looking for differences in restriction fragment lengths. A problem with this method (known as restriction fragment length polymorphism mapping or RFLP mapping) is its inability to detect mutations that do not affect cleavage with a restriction endonuclease. One study reported that only 0.7% of the mutational variants estimated to be present in a 40,000 base pair region of human DNA were detected using RFLP analysis. Jeffreys, *Cell,* 18:1–18 (1979).

Single base mutations have been detected by differential hybridization techniques using allele-specific oligonucleotide (ASO) probes. Saiki et al., *Proc. Natl. Acad. Sci. USA,* 86: 6230–6234 (1989). Mutations are identified on the basis of the higher thermal stability of the perfectly-matched probes as compared to mismatched probes. Disadvantages of this approach for mutation analysis include: (1) the requirement for optimization of hybridization for each probe, and (2) the nature of the mismatch and the local sequence impose limitations on the degree of discrimination of the probes. In practice, tests based only on parameters of nucleic acid hybridization function poorly when the sequence complexity of the test sample is high (e.g., in a heterogeneous biological sample). This is partly due to the small thermodynamic differences in hybrid stability generated by single nucleotide changes. Therefore, nucleic acid hybridization is generally combined with some other selection or enrichment procedure for analytical and diagnostic purposes.

In enzyme-mediated ligation methods, a mutation is interrogated by two oligonucleotides capable of annealing immediately adjacent to each other on a target DNA or RNA molecule, one of the oligonucleotides having its 3' end complementary to the point mutation. Adjacent oligonucleotide sequences are only covalently attached when both oligonucleotides are correctly base-paired. Thus, the presence of a point mutation is indicated by the ligation of the two adjacent oligonucleotides. Grossman et al., *Nucleic Acid Research,* 22: 4527–4534 (1994). However, the usefulness of this method for detection is compromised by high backgrounds which arise from tolerance of certain nucleotide mismatches or from non-template directed ligation reactions. Barringer et. al., *Gene,* 89: 117–122 (1990).

A number of detection methods have been developed which are based on a template-dependent, primer extension reaction. These methods fall essentially into two categories: (1) methods using primers which span the region to be interrogated for the mutation, and (2) methods using primers which hybridizes proximally and upstream of the region to be interrogated for the mutation.

In the first category, Caskey and Gibbs [U.S. Pat. No. 5,578,458] report a method wherein single base mutations in target nucleic acids are detected by competitive oligonucleotide priming under hybridization conditions that favor the binding of the perfectly-matched primer as compared to one with a mismatch. Vary and Diamond [U.S. Pat. No. 4,851, 331] described a similar method wherein the 3' terminal nucleotide of the primer corresponds to the variant nucleotide of interest. Since mismatching of the primer and the template at the 3' terminal nucleotide of the primer inhibits elongation, significant differences in the amount of incorporation of a tracer nucleotide result under normal primer extension conditions.

It has long been known that primer-dependent DNA polymerases have, in general, a low replication error rate. This feature is essential for the prevention of genetic mistakes which would have detrimental effects on progeny. Methods in a second category exploit the high fidelity inherent in this enzymological reaction. Detection of mutations is based on primer extension and incorporation of detectable, chain-terminating nucleoside triphosphates. The high fidelity of DNA polymerases ensures specific incorporation of the correct base labelled with a reporter molecule. Such single nucleotide primer-guided extension assays have been used to detect aspartylglucosaminuria, hemophilia B, and cystic fibrosis; and for quantifying point mutations associated with Leber Hereditary Optic Neuropathy (LHON). See. e.g., Kuppuswamy et al., *Proc. Natl. Acad. Sci. USA,* 88:1143–1147 (1991); Syvanen et al., *Genomics,* 8: 684–692 (1990); Juvonen et al., *Human Genetics,* 93: 16–20 (1994); Ikonen et al., *PCR Meth. Applications,* 1: 234–240 (1992); Ikonen et al., *Proc. Natl. Acad. Sci. USA,* 88: 11222–11226 (1991); Nikiforov et al., *Nucleic Acids Research,* 22: 4167–4175 (1994).

Strategies based on primer extension require considerable optimization to ensure that only the perfectly annealed oligonucleotide functions as a primer for the extension reaction. The advantage conferred by the high fidelity of the polymerases can be compromised by the tolerance of nucleotide mismatches in the hybridization of the primer to the template. Any "false" priming will be difficult to distinguish from a true positive signal.

The selectivity and stability of the oligonucleotide primer extension assay is determined by the length of the oligonucleotide primer. Under typical reaction conditions, short primers (i.e., less than about a 15-mer) exhibit transient, unstable hybridization and, consequently, do not readily prime the extension reaction. Moreover, in a complex heterogeneous biological sample, short primers exhibit non-specific binding to a wide variety of perfectly-matched complementary sequences. Thus, because of their low stability and high non-specific binding, short primers are not very useful for reliable identification of a mutation at a known location. Therefore, detection methods based on primer extension assays use oligonucleotide primers ranging in length from 15-mer to 25-mer. See e.g., PCT Patent Publications WO 91/13075; WO 92/15712; and WO 96/30545. Lengthening the probe to increase stability, however, has the effect of diminishing selectivity. Due to the small thermodynamic differences in hybrid stability generated by single nucleotide changes, a single base mismatch usually does not affect binding efficiency of longer oligonucleotide primers. This tolerance of nucleotide mismatches in the hybridization of the primer to the template can result in significant levels of non-specific "false" priming in complex heterogeneous biological samples.

Methods in the art reduce the possibility of false priming by decreasing the sequence complexity of the test sample. Thus, genomic DNA is isolated from the biological sample and/or amplified with PCR using primers which flank the region to be interrogated. The primer extension analysis is then conducted on the purified PCR products. See PCT Patent Publications WO 91/13075; WO 92/15712; and WO 96/30545. Moreover, since considerable optimization is required to ensure that only the perfectly annealed oligonucleotide functions as a primer for the extension reaction, only limited multiplexing of the primer extension assays is possible. Krook et al., supra report that multiplexing can be achieved by using primers of different lengths and by monitoring the wild-type and mutant nucleotide at each mutation site in two separate single nucleotide incorporation reactions. Given that the selectivity and stability of the oligonucleotide primer extension assay is determined by the length of the oligonucleotide primer, the number of primers that can be tested simultaneously in a given reaction mixture is very limited. Accordingly, these methods are limited in scope due to low throughput.

Therefore, there is a need in the art for simple and efficient detection methods for reliable large-scale screening for a large number of genomic mutations in heterogeneous biological samples. Such methods are provided herein.

SUMMARY OF THE INVENTION

The present invention provides high-throughput screening methods for detecting and identifying genetic mutations or the presence of disease-causing microorganisms in an heterogeneous biological sample.

Genomic nucleic acid samples are isolated from a biological sample. Once isolated, the nucleic acids may be employed in the present invention without further manipulation. Alternatively, one or more specific regions present in the nucleic acids may be amplified by, for example, PCR. Amplification at this step provides the advantage of increasing the concentration of specific nucleic acid sequences within the target nucleic acid sequence population.

In one embodiment, the nucleic acids are bound to a solid-phase support. This allows the simultaneous processing and screening of a large number of samples. Non-limiting examples of supports suitable for use in the present invention include nitrocellulose or nylon filters, glass beads, magnetic beads coated with agents for affinity capture, treated or untreated microtiter plates, and the like. In a preferred embodiment, the support is a microtiter dish, having a multiplicity of wells. The use of such a support allows the simultaneous determination of a large number of samples and controls, and thus facilitates the analysis. Moreover, automated systems can be used to provide reagents to such microtiter dishes. In an alternative embodiment, methods of the invention are conducted in an aqueous phase.

Methods of the invention comprise conducting a single-base extension with a segmented primer. In a preferred embodiment, methods of the invention comprise hybridizing two probes adjacent to a site of suspected mutation, wherein neither probe alone is capable of being a primer for template-dependent extension, but wherein adjacent probes are capable of priming extension. In a preferred embodiment, methods of the invention comprise hybridizing to a target nucleic acid a probe having a length from about 5 bases to about 10 bases, wherein the probe hybridizes immediately upstream of a suspected mutation. Methods of the invention further comprise hybridizing a second probe upstream of the first probe, the second probe having a length from about 15 to about 100 nucleotides and having a 3' non-extendible nucleotide. The second probe is substantially contiguous with the first probe. Preferably, substantially contiguous probes are between 0 and about 1 nucleotide apart. A linker is preferably used where the first and second probes are separated by two or more nucleotides, provided the linker does not interfere with the nucleic acid extension reaction. Such linkers are known in the art and include, for example, peptide nucleic acids, DNA binding proteins, and ligation.

In an alternative embodiment, each segmented primers comprise a series of first oligonucleotide probes. No member of the series of the first probes is capable of being a primer for nucleic acid polymerization unless every member of said series hybridize simultaneously to substantially contiguous portions of the target nucleic acid, thereby forming a contiguous primer. In one embodiment, the segmented primers comprise three 8-mer first probes. In another embodiment, the segmented primers comprise four 6-mer first probes.

Methods of the invention further comprise conducting an extension reaction to add nucleotides to the segmented primer resulting from co-hybridization of the above-described probes in a template-dependent manner. In a preferred embodiment, first probes hybridized to a target nucleic acid are extended with a labelled terminal nucleotide whereas first probes hybridized to a wild-type or non-target nucleic acid are extended with an unlabelled terminal nucleotide. Labelled ddNTPs or dNTPs preferably comprise a "detection moiety" which facilitates detection of the short probes that have been extended with a labelled terminal nucleotide. Detection moieties are selected from the group consisting of fluorescent, luminescent or radioactive labels, enzymes, haptens, and other chemical tags such as biotin which allow for easy detection of labelled extension products by, for example, spectrophotometric methods. In a preferred embodiment, In a preferred embodiment, several cycles of extension reactions are conducted in order to amplify the assay signal. Extension reactions are conducted in the presence of an excess of first and second probes, labelled dNTPs or ddNTPs, and heat-stable polymerase. Once an extension reaction is completed, the first and second probes bound to target nucleic acids are dissociated by heating the reaction mixture above the melting temperature of the hybrids. The reaction mixture is then cooled below the melting temperature of the hybrids and first and second probes are permitted to associate with target nucleic acids for another extension reaction. In a preferred embodiment, 10 to 50 cycles of extension reactions are conducted. In a most preferred embodiment, 30 cycles of extension reactions are conducted.

Finally, methods of the invention further comprise isolating and sequencing the extended first probes. First probes preferably comprise a "separation moiety" that facilitates the isolation of these probes. Non-limiting examples of separation moieties include hapten, biotin, and digoxigenin. In a preferred embodiment, first probes comprising a separation moiety are immobilized to a solid support having affinity for the separation moiety (e.g., coated with anti-hapten, avidin, streptavidin, or anti-digoxigenin). The solid support is selected from the group consisting of glass, plastic, and paper. The support is fashioned as a column, bead, dipstick, or test tube. In a preferred embodiment, the separation moiety is incorporated in the labelled ddNTPs or dNTPs and only first probes extended with a labelled ddNTP or dNTP are immobilized to the support. As such, labelled first probes are isolated from unextended first probes and second probes. In an alternative preferred embodiment, the separation moiety is incorporated in the all first probes, provided the separation moiety does not interfere with the first probe's ability to hybridize with template and to be extended. By incorporating the separation moiety in the first probes, all first probes are immobilized to a solid support. First probes are isolated from second probes by one or more washing steps.

Labelled first probes are then sequenced to identify a mutation or disease-causing microorganism. In one embodiment, the immobilized probes are directly subjected to sequencing, using for example, chemical methods standard in the art. In other embodiments, the labelled first probes are removed from the solid support and sequencing of labelled first probes is performed in aqueous solution. The isolated first probes are contacted with a multiplicity of complementary oligonucleotides. In one embodiment, enzymatic sequencing is performed using the isolated first probes as primers and the complementary oligonucleotides as templates. In an alternative embodiment, a single base extension reaction is performed using the isolated first probes as primers and the complementary oligonucleotides as templates. The sequence of the extension product is determined by enzymatic sequencing. The sequence of the extended labelled first probes identifies the genetic mutations or the disease-causing microorganisms present in the sample.

Methods disclosed herein may be used to detect mutations such as insertions, deletions, and substitutions. Nucleic acid samples that can be screened with the methods of the present invention include human nucleic acid samples.

Methods disclosed herein may be used to detect mutations associated with diseases such as cancer. Additionally, methods of the invention may be used to detect a deletion or a base substitution mutation causative of a metabolic error, such as complete or partial loss of enzyme activity.

In another embodiment, the specific nucleic acid sequence comprises a portion of a particular gene or genetic locus in the patient's genomic nucleic acid known to be involved in a pathological condition or syndrome. Non-limiting examples include cystic fibrosis, Tay-Sachs disease, sickle-cell anemia, β-thalassemia, and Gaucher's disease.

In yet another embodiment, the specific nucleic acid sequence comprises part of a particular gene or genetic locus that may not be known to be linked to a particular disease, but in which polymorphism is known or suspected.

In yet another embodiment, the specific nucleic acid sequence comprises part of a foreign genetic sequence e.g. the genome of an invading microorganism. Non-limited examples include bacteria and their phages, viruses, fungi, protozoa, and the like. The present methods are particularly applicable when it is desired to distinguish between different variants or strains of a microorganism in order to choose appropriate therapeutic interventions.

Further aspects and advantages of the invention are apparent upon consideration of the following detailed description thereof.

DETAILED DESCRIPTION OF THE INVENTION

Figure 1:
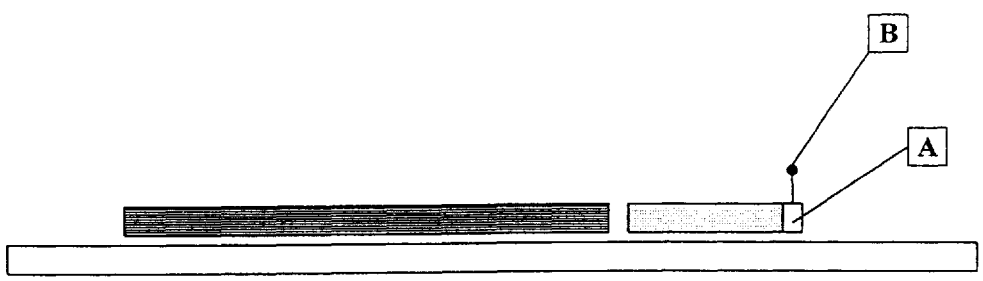
FIG. 1 is a diagram depicting the use of a segmented primer in a single base extension reaction for the detection of single base polymorphisms. The white bar represents the template, the dark gray bar represents second probe which hybridizes to a region on the template that is substantially contiguous with the first probe (light gray). The site suspected to be a single base mutation is labelled A. The detectable label is marked B.

The present invention provides a high-throughput method for detecting and identifying specific nucleic acid sequences in biological samples. Methods disclosed herein may be used to detect and identify mutations associated with diseases such as cancer, deletions or a base substitution mutations causative of a metabolic error, such as complete or partial loss of enzyme activity, portions of a particular gene or genetic locus in the patient's genomic nucleic acid known to be involved in a pathological condition or syndrome, or part of a foreign genetic sequence e.g. the genome of an invading disease-causing microorganism.

Methods of the invention comprise conducting a single-base extension with a segmented primer. In a preferred embodiment, the segmented primer comprises a short first probe and a longer second probe capable of hybridizing to substantially contiguous portions of the target nucleic acid. The two probes are exposed to a sample under conditions that do not favor the hybridization of short first probe in the absence of longer second probe. Factors affecting hybridization are well known in the art and include temperature, ion concentration, pH, probe length, and probe GC content. A first probe, because of its small size, hybridizes numerous places in an average genome. For example, any given 8-mer occurs about 65,000 times in the human genome. However, an 8-mer has a low melting temperature ($T_m$) and a single base mismatch greatly exaggerates this instability. A second probe, on the other hand, is larger than the first probe and will have a higher $T_m$. A 20-mer second probe, for example, typically hybridizes with more stability than an 8-mer. However, because of the small thermodynamic differences in hybrid stability generated by single nucleotide changes, a longer probe will form a stable hybrid but will have a lower selectivity because it will tolerate nucleotide mismatches. Accordingly, under unfavorable hybridization conditions for the first probe (e.g., 10–40° C. above first probe $T_m$), the first probe hybridizes with high selectivity (i.e., hybridizes poorly to sequence with even a single mismatch), but forms unstable hybrids when it hybridizes alone (i.e., not in the presence of a second probe). The second probe will form a stable hybrid but will have a lower selectivity because of its tolerance of mismatches.

The extension reaction in the present invention will not occur absent contiguous hybridization of the first and second probes. A first (proximal) probe alone is not a primer for template-based nucleic acid extension because it will not form a stable hybrid under the reaction conditions used in the assay. Preferably, the first probe comprises between about 5 and about 10 nucleotides. The first probe hybridizes adjacent to a nucleic acid suspected to be mutated. A second (distal) probe in mutation identification methods of the invention hybridizes upstream of the first probe and to a substantially contiguous region of the target (template). The second probe alone is not a primer of template-based nucleic acid extension because it comprises a 3' non-extendible nucleotide. The second probe is larger than the first probe, and is preferably between about 15 and about 100 nucleotides in length.

According to methods of the invention, template-dependent extension takes place only when a first probe hybridizes next to a second probe. When this happens, the short first probe hybridizes immediately adjacent to the site of the suspected single base mutation. The second probe hybridizes in close proximity to the 5' end of the first probe. The presence of the two probes together increases stability due to cooperative binding effects. Together, the two probes are recognized by polymerase as a primer. This system takes advantage of the high selectivity of a short probe and the hybridization stability imparted by a longer probe in order to generate a primer that hybridizes with the selectivity of a short probe and the stability of a long probe. Accordingly, there is essentially no false priming with segmented primers. Since the tolerance of mismatches by the longer second probe will not generate false signals, several segmented primers can be assayed in the same reaction, as long as the hybridization conditions do not permit the extension of short first probes in the absence of the corresponding longer second probes. Moreover, due to their increased selectivity for target, methods of the invention may be used to detect and identify a target nucleic acid that is available in small proportion in a sample and that would normally have to be amplified by, for example, PCR in order to be detected.

By requiring hybridization of the two probes, false positive signals are reduced or eliminated. As such, the use of segmented oligonucleotides eliminates the need for careful optimization of hybridization conditions for individual probes, as presently required in the art, and permits extensive multiplexing. Several segmented oligonucleotides can be used to probe several target sequences assayed in the same reaction, as long as the hybridization conditions do not permit stable hybridization of short first probes in the absence of the corresponding longer second probes.

The first and second probes hybridize to substantially contiguous portions of the target. For purposes of the present invention, substantially contiguous portions are those that are close enough together to allow hybridized first and second probes to function as a single probe (e.g., as a primer of nucleic acid extension). Substantially contiguous portions are preferably between zero (i.e., exactly contiguous so there is no space between the portions) nucleotides and about one nucleotide apart. A linker is preferably used where the first and second probes are separated by two or more nucleotides, provided the linker does not interfere with the assay (e.g., nucleic acid extension reaction). Such linkers are known in the art and include, for example, peptide nucleic acids, DNA binding proteins, and ligation. It has now been realized that the adjacent probes bind cooperatively so that the longer, second probe imparts stability on the shorter, first probe. However, the stability imparted by the second probe does not overcome the selectivity (i.e., intolerance of mismatches) of the first probe. Therefore, methods of the invention take advantage of the high selectivity of the short first probe and the hybridization stability imparted by the longer second probe.

Thus, in a preferred embodiment, first and second probes are hybridized to substantially contiguous regions of target, wherein the first probe is immediately adjacent and upstream of a site of suspected mutation, for example, a single base mutation. The sample is then exposed to dideoxy nucleic acids that are complements of possible mutations at the suspected site. For example, if the wild-type nucleic acid at a known site is adenine, then dideoxy adenine, dideoxy cytosine, and dideoxy guanine are placed into the sample. Preferably, the dideoxy nucleic acids are labelled. Deoxynucleotides may alternatively be used if the reaction is stopped after the addition of a single nucleotide. Polymerase, either endogenously or exogenously supplied, catalyzes incorporation of a dideoxy base on the first probe. Detection of label indicates that a non-wild-type (i.e., mutant) base has been incorporated, and there is a mutation at the site adjacent the first probe. Alternatively, methods of the invention may be practiced when the wild-type sequence is unknown. In that case, the four common dideoxy nucleotides are differentially labelled. Appearance of more than one label in the assay described above indicates a mutation may exist.

Deoxynucleotides may be used as the detectable single extended base in any of the reactions described above that require single base extension. However, in such methods, the extension reaction must be stopped after addition of the single deoxynucleotide. Such methods may be employed regardless of whether a specific mutation is known (i.e., C→G). Moreover, the extension reaction need not be terminated after the addition of only one deoxynucleotide if only one labelled species of deoxynucleotide is made available in the sample for detection of the single base mutation. This method may actually enhance signal if there is a nucleotide repeat including the interrogated single base position.

In an alternative preferred embodiment, a segmented oligonucleotide comprises a series of first probes, wherein sufficient stability is only obtained when all members of the segmented oligonucleotide simultaneously hybridize to substantially contiguous portions of a nucleic acid. It has now been realized that, although short probes exhibit transient, unstable hybridization, adjacent short probes bind cooperatively and with greater stability than each individual probe. Together, a series of adjacently-hybridized first probes will have greater stability than individual probes or a subset of probes in the series. For example, in an extension reaction with a segmented primer comprising a series of three first probes (i.e., three short probes with no terminal nucleotide capable of hybridizing to a substantially contiguous portion of a nucleic acid upstream of the target nucleic acid), the concurrent hybridization of the three probes will generate sufficient cooperative stability for the three probes to prime nucleic acid extension and the short probe immediately adjacent to a suspected mutation will be extended. Thus, segmented probes comprising a series of short first probes offer the high selectivity (i.e., intolerance of mismatches) of short probes and the stability of longer probes.

In a preferred embodiment, target nucleic acids are immobilized to a solid support prior to exposing the target nucleic acids to segmented primers and conducting an extension reaction. Once the nucleic acid samples are immobilized, the samples are washed to remove non-immobilized materials. The nucleic acid samples are then exposed to one or more set of segmented primers according to the invention. Once the single-base extension reaction is completed, the first probes extended with a labelled ddNTP or dNTP are preferably isolated from unextended probes and probes extended with an unlabelled ddNTPs or dNTP. The bound first and second probes are eluted from the support-bound target nucleic acid. Elution may be accomplished by any means known in the art that destabilizes nucleic acid hybrids (i.e., lowering salt, raising temperature, exposure to formamide, alkali, etc.). In a preferred embodiment, the first and second probes bound to target nucleic acids are dissociated by incubating the target nucleic acid-segmented primer complexes in water, and heating the reaction above the melting temperature of the hybrids and the extended first probes are isolated. In an alternative preferred embodiment, the extension reaction is conducted in an aqueous solution. Once the single-base extension reaction is completed, the oligonucleotide probes are dissociated from target nucleic acids and the extended first probes are isolated. In an alternative embodiment, the nucleic acids remain in aqueous phase.

In a preferred embodiment, several cycles of extension reactions are conducted in order to amplify the assay signal. Extension reactions are conducted in the presence of an excess of first and second probes, labelled dNTPs or ddNTPs, and heat-stable polymerase. Once an extension reaction is completed, the first and second probes bound to target nucleic acids are dissociated by heating the reaction mixture above the melting temperature of the hybrids. The reaction mixture is then cooled below the melting temperature of the hybrids and first and second probes permitted to associate with target nucleic acids for another extension reaction. In a preferred embodiment, 10 to 50 cycles of extension reactions are conducted. In a most preferred embodiment, 30 cycles of extension reactions are conducted.

Finally, methods of the invention comprise isolating and sequencing the extended first probes. A "separation moiety" such as, for example, hapten, biotin, or digoxigenin is used for the isolation of extended first probes. In a preferred embodiment, first probes comprising a separation moiety are immobilized to a solid support having affinity for the separation moiety (e.g., coated with anti-hapten, avidin, streptavidin, or anti-digoxigenin). Non-limiting examples of supports suitable for use in the present invention include nitrocellulose or nylon filters, glass beads, magnetic beads coated with agents for affinity capture, treated or untreated microtiter plates, and the like.

In a preferred embodiment, the separation moiety is incorporated in the labelled ddNTPs or dNTPs. By immobilizing eluted first probes extended with a labelled ddNTP or dNTP to a solid support, labelled first probes are isolated from unextended first probes and second probes, and first probes extended with an unlabelled ddNTPs by one or more washing steps.

In an alternative preferred embodiment, the separation moiety is incorporated in the first probes, provided the separation moiety does not interfere with the first probe's ability to hybridize with template and to be extended. Eluted first probes are immobilized to a solid support and can be isolated from eluted second probes by one or more washing steps.

The labelled first probes are then sequenced to identify the detected mutation or disease-causing microorganism. In one embodiment, the immobilized probes are directly subjected to sequencing, using a chemical method standard in the art. In other embodiments, the immobilized labelled first probes are removed from the solid support and sequencing of labelled first probes is performed in aqueous solution.

For purposes of exemplification, the following provides details of the use of methods according to the present invention in colon cancer detection. Inventive methods are especially useful in the early detection of a mutation. Accordingly, while exemplified in the following manner, the invention is not so limited and the skilled artisan will appreciate its wide range of applicability upon consideration thereof.

Exemplary Methods for Detection of Colon Cancer or Precancer

I. Sample Preparation

In accordance with the present invention, the target nucleic acid represents a sample of nucleic acid isolated from a patient. This nucleic acid may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, and tissue exudates at the site of infection or inflammation.

In a preferred embodiment, the sample is a cross-section of stool. A preferred method for preparing a cross-section of stool is provided in co-owned, patent application Ser. No. 08/699,678 issued as U.S. Pat. No. 5,741,650, incorporated by reference herein. As stool passes through the colon, it adheres cells and cellular debris sloughed from colonic epithelial cells. Similarly, cells and cellular debris are sloughed by a colonic polyp (comprising mutated DNA). However, only the portion of stool making contact with the polyp will adhere sloughed cells. It is therefore necessary to obtain at least a cross-section of stool in order to ensure that the stool sample contains a mixture of all sloughed cells, including those sloughed by presumptive cancer cells (e.g., polyps).

After sample preparation, the sample is homogenized in an appropriate buffer, such as phosphate buffered saline comprising a salt, such as 20–100 mM NaCl or KCl, and a detergent, such as 1–10% SDS or Triton™, and/or a proteinase, such as proteinase K. An especially-preferred buffer is a Tris-EDTA-NaCl buffer, incorporated by reference herein. The buffer may also contain inhibitors of DNA and RNA degrading enzymes. Double-stranded DNA in the sample is melted (denatured to form single-stranded DNA) by well-known methods See, e.g., Gyllensten et al., in *Recombinant DNA Methodology II*, 565–578 (Wu, ed., 1995), incorporated by reference herein. DNA is then isolated from the cell source or body fluid using any of the numerous methods that are standard in the art. See, Smith-Ravin et al., *Gut*, 36 81–86 (1995), incorporated by reference herein. It will be understood that the particular method used to extract DNA will depend on the nature of the source.

Once extracted, the target nucleic acid may be employed in the present invention without further manipulation. Alternatively, one or more specific regions present in the target nucleic acid may be amplified by PCR. In this case, the amplified regions are specified by the choice of particular flanking sequences for use as primers. Amplification at this step provides the advantage of increasing the concentration of specific nucleic acid sequences within the target nucleic acid sequence population.

In one embodiment, the target nucleic acid, with or without prior amplification of particular sequences, is bound to a solid-phase support. This allows the simultaneous processing and screening of a large number of patient samples. Non-limiting examples of supports suitable for use in the present invention include nitrocellulose or nylon filters, glass beads, magnetic beads coated with agents for affinity capture, treated or untreated microtiter plates, and the like. The conventional 96-well microtiter dishes used in diagnostic laboratories and in tissue culture are a preferred support. In a preferred embodiment, the support is a microtiter dish, having a multiplicity of wells. The use of such a support allows the simultaneous determination of a large number of samples and controls, and thus facilitates the analysis. Moreover, automated systems can be used to provide reagents to such microtiter dishes. It will be understood by a skilled practitioner that the method by which the target nucleic acid is bound to the support will depend on the particular matrix used. For example, binding of DNA to nitro-cellulose can be achieved by simple adsorption of DNA to the filter, followed by baking the filter at 75°–80° C. under vacuum for 15 min-2 h. Alternatively, charged nylon membranes can be used that do not require any further treatment of the bound nucleic acid. Beads and microtiter plates that are coated with avidin or streptavidin can be used to bind target nucleic acid that has had biotin attached (via e.g. the use of biotin-conjugated PCR primers). In addition, antibodies can be used to attach target nucleic acids to any of the above solid supports by coating the surfaces with the antibodies and incorporating an antibody-specific hapten into the target nucleic acids. The target nucleic acids can also be attached directly to any of the above solid supports by epoxide/amine coupling chemistry. See Eggers et al. *Advances in DNA Sequencing Technology,* SPIE conference proceedings (1993). Once the nucleic acid samples are immobilized, the samples are washed to remove non-immobilized materials. The nucleic acid samples are then exposed to one or more set of segmented primers according to the invention. In an alternative embodiment, the nucleic acids remain in aqueous phase.

II Preparation of Segmented Primers

Genomic regions suspected to contain one or more mutations are identified by reference to a nucleotide database, such as GenBank, EMBL, or any other appropriate database or publication, or by sequencing. For cancer detection, genetic mutations in a number of oncogenes and tumor suppressor genes are known. Duffy, *Clin. Chem.,* 41: 1410–1413 (1993). Preferred genes for use in mutation detection methods of the invention include one or more oncogenes and/or one or more tumor suppressor genes. Specifically preferred genes include the ras oncogenes, p53, dcc, apc, mcc, and other genes suspected to be involved in the development of an oncogenic phenotype.

As will be described below, methods of the invention permit the detection of a mutation at a locus in which there is more than one nucleotide to be interrogated. Moreover, methods of the invention may be used to interrogate a locus in which more than one single base mutation is possible. Once regions of interest are identified, at least one segmented primer is prepared to detect the presence of a suspected mutation. A segmented primer comprises at least two oligonucleotide probes, a first probe and a second probe, which are capable hybridizing to substantially contiguous portions of a nucleic acid.

A first probe of the invention preferably has a length of from about 5 to about 10 nucleotides, more preferably between about 6 and about 8 nucleotides, and most preferable about 8 nucleotides. A second probe of the invention has a preferable length of between about 15 and 100 nucleotides, more preferably between about 15 and 30 nucleotides, and most preferably about 20 nucleotides. Further, a second probe is incapable of being a primer for template-dependent nucleic acid synthesis absent a first probe because it has a 3' terminal nucleotide that is non-extendible. Preferred non-extendible 3' terminal nucleotides include dideoxy nucleotides, C3 spacers, a 3' inverted base, biotin, or a modified nucleotide. Although, longer probes have a lower selectivity because of their tolerance of nucleotide mismatches, second probes are non-extendible and will not produce false priming in the absence of the proximal probe.

In an alternative embodiment, a segmented primer comprises a series of first probes, wherein each member of the series has a length of from about 5 to about 10 nucleotides, and most preferable about 6 to about 8 nucleotides. Although the first probes do not have a terminal nucleotide, nucleic acid extension will not occur unless all members of the series are hybridized to substantially contiguous portions of a nucleic acid.

The oligonucleotide probes of the segmented primer may be natural or synthetic, and may be synthesized enzymatically in vivo, enzymatically in vitro, or non-enzymatically in vitro. Probes for use in methods of the invention are preferably selected from oligodeoxyribonucleotides, oligoribonucleotides, copolymers of deoxyribonucleotides and ribonucleotides, peptide nucleic acids (PNAs), and other functional analogues. Peptide nucleic acids are well-known. See Pluskal, et al., *The FASEB Journal,* Poster #35 (1994). They are synthetic oligoamides comprising repeating amino acid units to which adenine, cytosine, guanine, thymine or uracil are attached. See Egholm, et al., *Nature,* 365: 566–568 (1993); Oerum, et al. *Nucl. Acids Res.,* 23: 5332–36 (1993); *Practical PNA: Identifying Point Mutations by PNA Directed PCR Clamping,* PerSeptive Biosystems Vol. 1, Issue 1 (1995). Peptide nucleic acid synthons and oligomers are commercially available form PerSeptive Biosystems, Inc., Framingham, Mass. See, e.g., PCT publications EP 92/01219, EP 92/01220, U.S. Pat. No. 92/10921. In many applications, PNA probes are preferred to nucleic acid probes because, unlike nucleic acid/nucleic acid duplexes, which are destabilized under conditions of low salt, PNA/nucleic acid duplexes are formed and remain stable under conditions of very low salt. Additionally, because PNA/DNA complexes have a higher thermal melting point than the analogous nucleic acid/nucleic acid complexes, use of PNA probes can improve the reproducibility of blotting assays.

For exemplification, probes designed to detect mutations in the K-ras gene are provided below. According to methods of the invention, probes complementary to either portions of the coding strand or to portions of the non-coding strand may be used. For illustration, probes useful for detection of mutations in the coding strand are provided below. Mutations in K-ras frequently occur in the codon for amino acid 12 of the expressed protein. Several of the possible probes for detection of mutations at each of the three positions in codon 12 are shown below.

The wild-type codon 12 of the K-ras gene and its upstream nucleotides are:

wild-type template  3'-TATTTGAACACCATCAACCTCGA<u>CCA</u>-5'  (SEQ ID NO: 1)

The three nucleotides encoding amino acid 12 are underlined. First probes and second probes capable of interrogating the three nucleotides coding for amino acid 12 of the K-ras gene are provided below. First probe A is a first probe as described generally above, and has a sequence complementary to the nucleotides immediately upstream of the first base in codon 12 (i.e., immediately adjacent to the cytosine at codon position 1). Second probe A is a second probe as generally described above. It is complementary to a sequence that is substantially contiguous (here, exactly contiguous) with the sequence to which the first probe A is complementary. The bolded nucleotide in each of the second probes shown below is the non-extendible 3' terminal nucleotide. Hybridization of first and second probes suitable for detection of a mutation in the first base of K-ras codon 12 are shown below:

| | | |
|---|---|---|
| second probe A | 5'-ATAAACTTGTGGTAG | (SEQ ID NO: 2) |
| first probe A | TTGGAGCT | (SEQ ID NO: 3) |
| wild-type template | 3'-TATTTGAACACCATCAACCTCGA<u>CCA</u>-5' | (SEQ ID NO: 1) |

Detection of a mutation in the second base in codon 12 may be performed by using the same second probe as above (second probe A), and a first probe, identified as first probe B below, that is complementary to a sequence terminating immediately adjacent (3') to the second base of codon 12. Hybridization of probes suitable for detection of a mutation in the second base of codon 12 are shown below:

| | | |
|---|---|---|
| second probe A | 5'-ATAAACTTGTGGTAG | (SEQ ID NO: 2) |
| first probe B | TGGAGCTG | (SEQ ID NO: 4) |
| wild-type template | 3'-TATTTGAACACCATCAACCTCGA<u>CCA</u>-5' | (SEQ ID NO: 1) |

Detection of a mutation at the third position in codon 12 is accomplished using the same second probe as above, and first probe C, which abuts the third base of codon 12. Hybridization of probes suitable for detection of a mutation in the third base of codon 12 are shown below

| | | |
|---|---|---|
| second probe A | 5'-ATAAACTTGTGGTAG | (SEQ ID NO: 2) |
| first probe C | GGAGCTGG | (SEQ ID NO: 6) |
| wild-type template | 3'-TATTTGAACACCATCAACCTCGA<u>CCA</u>-5' | (SEQ ID NO: 1) |

In methods for detection of mutations at the second and third nucleotides of codon 12 described above, the second probe is 1 and 2 nucleotides, respectively, upstream of the region to which the first probe hybridizes. Alternatively, second probes for detection of the second and third nucleotides of codon 12 may directly abut (i.e., be exactly contiguous with) their respective first probes. For example, an alternative second probe for detection of a mutation in the third base of codon 12 in K-ras is:

5'-ATAAACTTGTGGTAGTT    (SEQ ID NO: 5)

The detection of mutations can also be accomplished with a segmented primer comprising a series of at least three first probes. A series of first probes suitable for detection of a mutation in the third base of codon 12 is shown below:

| | | |
|---|---|---|
| first probe X | 5'-ATAAACTT | (SEQ ID NO: 7) |
| first probe Y | TGGTAGTT | (SEQ ID NO: 8) |
| first probe Z | GGAGCTGG | (SEQ ID NO: 6) |
| wild-type template | 3'-TATTTGAACACCATCAACCTCGA<u>CCA</u>-5' | (SEQ ID NO: 1) |

III Single base primer extension assays

First and second probes are exposed to sample under hybridization conditions that do not favor the hybridization of the short first probe in the absence of the longer second probe. Factors affecting hybridization are well known in the art and include raising the temperature, lowering the salt concentration, or raising the pH of the hybridization solution. Under unfavorable hybridization conditions (e.g., at a temperature 30°–40° C. above first probe $T_m$), first probe forms an unstable hybrid when hybridized alone (i.e., not in the presence of a second probe) and will not prime the extension reaction. The longer, second probe, having a higher $T_m$, will form a stable hybrid with the template and, when hybridized to substantially contiguous portions of the nucleic acid, the second probe will impart stability to the shorter first probe, thereby forming a contiguous primer.

Following the hybridization, the sample may optionally be washed to remove unhybridized probes. In a preferred embodiment, a modification of the dideoxy chain termination method as reported in Sanger, *Proc. Nat'l Acad. Sci. (USA)*, 74: 5463–5467 (1977), incorporated by reference herein, is then used to detect the presence of a mutation. The method involves using at least one of the four common 2', 3' -dideoxy nucleoside triphosphates (ddATP, ddCTP, ddGTP, and ddTTP). A detectable detection moiety can be attached to the dideoxy nucleoside triphosphates (ddNTPs) according to methods known in the art. A DNA polymerase, such as Sequenase™ (Perkin-Elmer), is also added to the sample mixture. Using the substantially contiguous first and second probes as a primer, the polymerase adds one ddNTP to the 3' end of the first probe, the incorporated ddNTP being complementary to the nucleotide that exists at the single-base polymorphic site. Because the ddNTPs have no 3' hydroxyl, further elongation of the hybridized probe will not occur. Chain termination will also result where there is no available complementary ddNTP (or deoxynucleoside triphosphates) in the extension mixture. After completion of the single base extension reaction, extension products are isolated and detected.

Also in a preferred embodiment, labelled deoxynucleotides may be used for detection if either the extension reaction is stopped after addition of only one nucleotide or if only one labelled nucleotide, corresponding to the complement of the expected mutation, is exposed to the sample.

In the simplest embodiment of the invention, the nucleoside triphosphate mixture contains just the labelled ddNTP or dNTP complementary to the known mutation. For example, to interrogate a sample for a C→A mutation in the first nucleotide of codon 12 of the K-ras gene, second probe A and first probe A are exposed to an extension reaction mixture containing labelled ddTTP or dTTP. The incorporation of a labelled ddTTP or dTTP in first probe A indicates the presence of a C→A mutation in the first nucleotide of codon 12 of the K-ras gene in the sample tested. First probe A co-hybridized with second probe A to a wild-type template will not be extended or, alternatively, will be extended with unlabelled ddGTP or dGTP if available in the reaction mixture.

Given the large number of mutations that have been associated with colorectal cancer, a detection method for this disease preferably screens a sample for the presence of a large number of mutations simultaneously in the same reaction (e.g., apc, K-ras, p53, dcc, MSH2, and DRA). As described above, only very limited multiplexing is possible with detection methods of the prior art. Since methods of the present invention eliminate false positive signals resulting from the tolerance of mismatches of the longer second probes, the use of segmented oligonucleotide avoids the need for optimization of hybridization conditions for individual probes and permits extensive multiplexing. Several segmented primers can be assayed in the same reaction, as long as the hybridization conditions do not permit stable hybridization of short first probes in the absence of the corresponding longer second probes.

In a preferred embodiment, the primer extension reactions are conducted in four separate reaction mixtures, each having an aliquot of the biological sample, a polymerase, and the three labelled complementary non-wild-type ddNTPs (or dNTPs). Optionally, the reaction mixtures may also contain the unlabelled complementary wild-type ddNTP (or dNTP). The segmented primers are multiplexed according to the wild-type template. In the present examplification, the first two nucleotides coding for amino acid 12 of the K-ras gene are cysteines. Accordingly, second probe A and first probes A and B are added to a reaction mixture containing labelled ddATP (or dATP), ddTTP (or dTTP), and ddCTP (or dCTP). Second probe C and first probe C are added to a reaction mixture containing labelled ddATP (or dATP), ddCTP (or dCTP), and ddGTP (or dGTP). Any incorporation of a labelled ddNTP in a first probe indicates the presence of a mutation in codon 12 of the K-ras gene in the sample. This embodiment is especially useful for the interrogation of loci that have several possible mutations, such as codon 12 of K-ras.

In an alternative preferred embodiment, the primer extension reactions are conducted in four separate reaction mixtures, each containing only one labelled complementary non-wild-type ddNTP or dNTP and, optionally, the other three unlabelled ddNTPs or dNTPs. Segmented primers can be thus be exposed only to the labelled ddNTP or dNTP complementary to the known mutant nucleotide or, alternatively, to all three non-wild-type labelled ddNTPs or dNTPs. In the K-ras example provided above, if the first nucleotide of K-ras codon 12 is interrogated for a known C→G mutation, first probe A and second probe A are added to only one reaction mixture, the reaction mixture containing labelled ddCTP (or dCTP). Optionally, methods of the invention may be practiced as described above using labelled deoxynucleotides.

However, since several mutations have been identified at codon 12 of the K-ras gene, the probes are exposed to all non-wild-type labelled ddNTPs or dNTPs. Thus, second probe A and first probes A and B are added to the three reaction mixtures containing labelled ddATP (or dATP), ddTTP (or dTTP), or ddCTP (or dCTP). Second probe C and first probe C are added to the three reaction mixtures containing one of labelled ddATP (or dATP), ddCTP (or dCTP), and ddGTP (or dGTP). Again, the extension of a first probe with a labelled terminal nucleotide indicates the presence of a mutation in codon 12 of the K-ras gene in the biological sample tested.

In a preferred embodiment, several cycles of extension reactions are conducted in order to amplify the assay signal. Extension reactions are conducted in the presence of an excess of first and second probes, labelled dNTPs or ddNTPs, and heat-stable polymerase. Once an extension reaction is completed, the first and second probes bound to target nucleic acids are dissociated by heating the reaction mixture above the melting temperature of the hybrids. The reaction mixture is then cooled below the melting temperature of the hybrids and first and second probes permitted to associate with target nucleic acids for another extension reaction. In a preferred embodiment, 10 to 50 cycles of extension reactions are conducted. In a most preferred embodiment, 30 cycles of extension reactions are conducted.

IV. Methods for Detection and Isolation of Labelled Nucleotides

Labelled ddNTPs or dNTPs preferably comprise a "detection moiety" which facilitates detection of the short first probes that have been extended with a labelled terminal nucleotide. Detection moieties are selected from the group consisting of fluorescent, luminescent or radioactive labels, enzymes, haptens, and other chemical tags such as biotin which allow for easy detection of labelled extension products. Fluorescent labels such as the dansyl group, fluorescein and substituted fluorescein derivatives, acridine derivatives, coumarin derivatives, pthalocyanines, tetramethylrhodamine, Texas Red®, 9-(carboxyethyl)-3-hydroxy-6-oxo-6H-xanthenes, DABCYL® and BODIPY® (Molecular Probes, Eugene, Oreg.), for example, are particularly advantageous for the methods described herein. Such labels are routinely used with automated instrumentation for simultaneous high throughput analysis of multiple samples.

Preferably, unbound first and second probes are removed following hybridization under conditions that preserve perfectly matched nucleic acid hybrids. Washing conditions (i.e., temperature, nature and concentration of salts, and time of washing) are determined empirically as described above.

At this stage, the presence of first probes that have been extended with a labelled terminal nucleotide may be determined before proceeding to the elution step (see below). The methods for detection will depend upon the label or tag incorporated into the first probes. For example, radioactively labelled or chemiluminescent first probes that have bound to the target nucleic acid can be detected by exposure of the filter to X-ray film. Alternatively, first probes containing a fluorescent label can be detected by excitation with a laser or lamp-based system at the specific absorption wavelength of the fluorescent reporter.

In a subsequent step, the bound first and second probes are eluted from the matrix-bound target nucleic acid. Elution may be accomplished by any means known in the art that destabilizes nucleic acid hybrids (i.e., lowering salt, raising temperature, exposure to formamide, alkali, etc.). In a preferred embodiment, the bound oligonucleotide probes are eluted by incubating the target nucleic acid-segmented primer complexes in water, and heating the reaction above the melting temperature of the hybrids.

In a preferred embodiment, first probes comprise a "separation moiety." Such separation moiety is, for example, hapten, biotin, or digoxigenin. Following the elution, first probes comprising a separation moiety are immobilized to a solid-phase matrix having affinity for the separation moiety (e.g., coated with anti-hapten, avidin, streptavidin, or anti-digoxigenin). Non-limiting examples of matrices suitable for use in the present invention include nitrocellulose or nylon filters, glass beads, magnetic beads coated with agents for affinity capture, treated or untreated microtiter plates, and the like.

In a preferred embodiment, the separation moiety is incorporated in the labelled ddNTPs or dNTPs. By immobilizing eluted first probes extended with a labelled ddNTP or dNTP to a solid matrix, labelled first probes are isolated from unextended first probes and second probes, and first probes extended with an unlabelled ddNTPs by one or more washing steps.

In an alternative preferred embodiment, the separation moiety is incorporated in the first probes, provided the separation moiety does not interfere with the first probe's ability to hybridize with template and be extended. Eluted first probes are immobilized to a solid support and can be isolated from eluted second probes by one or more washing steps.

V. Methods for Identification of Genetic Alterations

In one embodiment, the immobilized probes are directly subjected to sequencing, using a chemical method standard in the art (e.g., Maxam-Gilbert sequencing, Maxam and Gilbert, 1977, *Proc. Natl. Acad. Sci., USA*, 74:560).

In other embodiments, the immobilized labelled first probes are removed from the solid support and sequencing of labelled first probes is performed in aqueous solution. In one embodiment, the sequence of the labelled first probes is determined by sequence-specific reverse hybridization by exposing the labelled first probes to oligonucleotides corresponding to each of the multiple sequences being interrogated in the assay. Hybridization analysis can be accomplished by several methods known in the art, such as dot blots. See, Ausubel et al., *Short Protocols in Molecular Biology*, 3rd ed. (John Wiley & Sons, Inc., 1995). In a preferred embodiment, the oligonucleotides are immobilized to a solid support at defined locations (i.e., known positions). This immobilized array is sometimes referred to as a "DNA chip." The solid support can be a plate or chip of glass, silicon, or other material. The solid support can also be coated (e.g., with gold or silver) to facilitate attachment of the oligonucleotides to the surface of the solid support. Any of a variety of methods known in the art may be used to immobilize oligonucleotides to a solid support. A commonly used method consists of the non-covalent coating of the solid support with avidin or streptavidin and the immobilization of biotinylated oligonucleotide probes. The oligonucleotides can also be attached directly to the solid supports by epoxide/amine coupling chemistry. See Eggers et al. *Advances in DNA Sequencing Technology*, SPIE conference proceedings (1993).

In another embodiment, the sequence of the labelled first probe is read by the hybridization and assembly of positively hybridizing probes through overlapping portions. Drmanac et al., U.S. Pat. No. 5,202,231, incorporated herein by reference.

In yet another embodiment, first probes extended by a labelled dNTP are identified by enzymatic DNA sequencing (Sanger et al., 1977, *Proc. Natl. Acad. Sci., USA*, 74:5463). In this case, oligonucleotides are synthesized that contain DNA sequences complementary to the first probes and additional pre-determined co-linear sequences that act as sequence "tags." When incubated under Sanger sequencing conditions, the immobilized first probes hybridize to their complementary sequences and act as primers for the sequencing reaction. Determination of the resulting primed sequence "tag" then identifies the first probe(s) present in the reaction.

In a further embodiment, first probes extended by a labelled dNTP are amplified prior to the sequence identification. Labelled first probes are incubated with complementary oligonucleotides that contain a sequencing primer sequence with or without an additional "tag". Initial hybridization of a first probe to its complementary oligonucleotide allows the first probe to serve as the initial primer in a single extension reaction. The extension product is then used directly as template in a cycle sequencing reaction. Cycle sequencing of the extension products results in amplification of the sequencing products. In designing the complementary oligonucleotides, the sequencing primer is oriented so that sequencing proceeds through the first probe itself, or, alternatively, through the "tag" sequence. In the latter case, the determination of the "tag" sequence will identify the colinear first probe sequence. The amplified products are sequenced by a chemical method standard in the art or identified by sequence-specific reverse hybridization methods, as described above.

In practicing the present invention, it is not necessary to determine the entire sequence of the first probe or of the complementary tagged oligonucleotide. It is contemplated that 1, 2, or 3 sequencing reactions (instead of the four needed to obtain a complete sequence) will be effective in producing characteristic patterns (similar to "bar codes") to allow the immediate identification of the individual first probes. This approach is applicable to manual sequencing methods using radioactively labelled first probes, which produce analog or digitized autoradiograms, as well as to automated sequencing methods using non-radioactive reporter molecules, which produce digitized patterns. In either case, comparisons to an established data base can be performed electronically. Thus, by reducing the number of required sequencing reactions, the methods of the present invention facilitate the economical analysis of multiple samples.

The present invention accommodates the simultaneous screening of a large number of potential first probes in a single reaction. In practice, the actual number of segmented primers that are pooled for simultaneous hybridization is determined according to the diagnostic need. For example, in cystic fibrosis (CF), one particular mutation (Δ508) accounts for more than 70% of CF cases. This, a preliminary screening with a Δ508-specific segmented primers according to the present methods, followed by single base extension of the contiguous primers, and detection of the extended first probes, will identify and eliminate Δ508 alleles. In a second ("phase two") screening, a large number of segmented primers encoding other, less frequent, CF alleles is performed, followed by single base extension of the contiguous primers, and detection of the extended first probes as described above.

In other clinical situations, however, a single mutation that appears with as high a frequency as the Δ508 mutation in CF does not exist. Therefore, pools of segmented primers are determined only by the number of independent assays that would be needed in a phase two analysis on a pool positive sample.

In addition, in current clinical practice, different clinical syndromes, e.g. cystic fibrosis, thalassemia, and Gaucher's disease, are screened independently of each other. The present invention, by contrast, accommodates the simultaneous screening of large numbers of nucleic acids from different patients with a large number of first probes that are complementary to mutations in more than one potential disease-causing gene.

In the same manner, when clinical indicators suggest infection by a foreign agent or microorganism, the present invention provides for simultaneous screening for a large number of potential foreign nucleic acids. Furthermore, particular strains, variants, mutants, and the like of one or more microorganisms can also be distinguished by employing appropriate first probes in the first screening.

The methods of the present invention also make it possible to define potentially novel mutant alleles carried in the nucleic acid of a patient or an invading microorganism, by the use of randomly permuted segmented primers in phase one or phase two screening. In this embodiment, single base extension of contiguous primers and detection and isolation of extended first probes, followed by sequencing, reveals the precise mutant sequence.

The foregoing exemplifies practice of the invention in the context of multiple mutation detection using segmented primers. As disclosed herein, numerous additional aspects and advantages of the invention are apparent upon consideration of the disclosure and the specific exemplification. Accordingly, the invention is limited only by the scope of the appended claims.

What is claimed is:

1. A method for screening genomic nucleic acid samples to identify a nucleic acid mutation comprising the steps of:
  (i) isolating a plurality of genomic nucleic acids;
  (ii) exposing said nucleic acids to one or more segmented primers, each comprising a first primer having a length between 5 and 8 nucleotides, and a second primer having a length between 15 and 100 nucleotides and a 3' non-extendible nucleic acid, wherein said first and second primers hybridize to regions of a target nucleic acid that are separated by no more than one nucleotide on said target and wherein said second primer binds upstream of said first primer;
  (iii) conducting a template-based nucleic acid extension reaction, thereby to add a single terminal nucleotide to one or more of said first probes;
  (iv) isolating extended first probes; and
  (v) determining the sequence of said extended first probes; thereby to detect the presence or absence of a genetic alteration.

2. The method of claim 1, wherein said mutation is selected from the group consisting of insertions, deletions, and substitutions.

3. The method of claim 1, wherein said nucleic acid samples are human nucleic acids.

4. The method of claim 1, wherein said mutation is causative of a disease selected from the group consisting of cystic fibrosis, β-thalassemia, Tay-Sachs disease, sickle cell anemia, and Gaucher's disease.

5. The method of claim 1, wherein at least one of said target nucleic acids is amplified prior to said exposing step.

6. The method of claim 1, wherein said second probe is a peptide nucleic acid.

7. The method of claim 1, wherein said single terminal nucleotide is a haptenated non-wild-type nucleotide.

8. The method of claim 7, wherein said isolating step comprises:
   (i) dissociating extended first probes from target nucleic acids;
   (ii) immobilizing said extended first probes on a hapten-specific solid-phase support; and
   (iii) washing said solid-phase support to remove unbound first and second probes and terminal nucleotides.

9. The method of claim 1, wherein said determining step comprises chemical sequencing.

10. A method for screening genomic nucleic acid samples to identify a mutation comprising the steps of:
    (i) immobilizing a plurality of genomic nucleic acids on a solid phase support;
    (ii) exposing said immobilized nucleic acids to one or more segmented primers, each comprising a first primer having a length between 5 and 8 nucleotides and a second primer having a length between 15 and 100 nucleotides and a 3' non-extendible nucleic acid, wherein said first and second primers hybridize to regions of a target nucleic acid that are separated by no more than one nucleotide on said target and wherein said second primer binds upstream of said first primer;
    (iii) conducting a template-based nucleic acid extension reaction, thereby to add a single terminal nucleotide to one or more of said first probes;
    (iv) isolating extended first probes; and
    (v) determining the sequence of said extended first probes; thereby to detect the presence or absence of a genetic alteration.

11. The method of claim 10, wherein said solid-phase support is selected from the group consisting of nitrocellulose filter, nylon filter, magnetic beads, glass beads, and plastic.

12. The method of claim 10, wherein said first probe and said second probe form an exactly contiguous primer.

13. A method for high-throughput screening of genomic nucleic acid samples to identify one or more genetic alterations in one or more target nucleic acid sequences present in said samples, comprising the steps of:
    (i) isolating a plurality of genomic nucleic acids;
    (ii) exposing said nucleic acids to an excess amount of one or more segmented primers, each comprising a first primer having a length between 5 and 8 nucleotides, and a second primer having a length between 15 and 100 nucleotides and a 3' non-extendible nucleic acid, wherein said first and second primers hybridize to regions of a target nucleic acid that are separated by no more than one nucleotide on said target and wherein said second primer binds upstream of said first primer;
    (iii) conducting a template-based nucleic acid extension reaction in the presence of a heat-stable polymerase and an excess amount of labeled non-wild-type nucleotides, thereby to add a single labeled terminal nucleotide to one or more of said first probes;
    (iv) heating the extension reaction mixture of step (iii), thereby to dissociate said first probes and said second probes from said target nucleic acids;
    (v) cooling the extension reaction mixture of step (iv), thereby to expose said target nucleic acids to said excess amount of segmented primers;
    (vi) repeating step (iii);
    (vii) isolating extended labeled first probes; and
    (viii) determining the sequence of said extended labeled first probes; thereby to detect the presence or absence of a genetic alteration.

14. The method according to claim 13, wherein step (iv) to step (vi) are repeated 10 to 50 times.

15. The method according to claim 13, wherein step (iv) to step (vi) are repeated 30 times.

* * * * *